US008728968B2

(12) United States Patent
Gibson et al.

(10) Patent No.: US 8,728,968 B2
(45) Date of Patent: May 20, 2014

(54) SYNTHESIS OF BIOCERAMIC COMPOSITIONS

(75) Inventors: Iain Ronald Gibson, Aberdeen (GB); Janet Mabel Scott Skakle, Aberdeen (GB)

(73) Assignee: University Court of the University of Aberdeen, Aberdeen Aberdeenshire (GB)

( * ) Notice: Subject to any disclaimer, the term of this patent is extended or adjusted under 35 U.S.C. 154(b) by 349 days.

(21) Appl. No.: 12/812,181

(22) PCT Filed: Jan. 9, 2009

(86) PCT No.: PCT/GB2009/000059
§ 371 (c)(1),
(2), (4) Date: Sep. 30, 2010

(87) PCT Pub. No.: WO2009/087390
PCT Pub. Date: Jul. 16, 2009

(65) Prior Publication Data
US 2011/0021338 A1    Jan. 27, 2011

(30) Foreign Application Priority Data
Jan. 9, 2008    (GB) .................................. 0800335.2

(51) Int. Cl.
*C04B 35/03* (2006.01)
*C04B 35/00* (2006.01)
*A01N 59/26* (2006.01)
*C09K 3/00* (2006.01)

(52) U.S. Cl.
USPC .............. 501/123; 501/154; 424/602; 106/35

(58) Field of Classification Search
USPC .......... 501/123, 133, 154; 424/601, 602, 605; 106/35
See application file for complete search history.

(56) References Cited

U.S. PATENT DOCUMENTS

| 4,612,053 | A | 9/1986 | Brown et al. |
| 6,342,547 | B1 | 1/2002 | Mimura et al. |
| 6,846,493 | B2 * | 1/2005 | Pugh et al. ..................... 424/423 |
| 7,291,345 | B2 * | 11/2007 | Winterbottom et al. ...... 424/400 |
| 2007/0003634 | A1 * | 1/2007 | Gibson et al. ................. 424/602 |
| 2007/0134285 | A1 * | 6/2007 | Lynn et al. .................... 424/423 |

FOREIGN PATENT DOCUMENTS

| EP | 1584338 A2 | 10/2005 |
| JP | 03023245 A | 1/1991 |
| JP | 03033059 A | 2/1991 |
| JP | 04022003 A | 1/1992 |
| JP | 4022004 A | 1/1992 |
| WO | PCT/GB97/02325 | 3/1998 |

OTHER PUBLICATIONS

Vallet-Regi et al. Calcium phosphates as substitution of bone tissues. Progress in Solid State Chemistry 32 (2004) 1-31.*

(Continued)

*Primary Examiner* — Noah Wiese
(74) *Attorney, Agent, or Firm* — Bozicevic, Field & Francis LLP; Bret E. Field; Benjamin C. Pelletier

(57) ABSTRACT

A process for the synthesis of a bioceramic composition comprising calcium phosphosilicate (CPS, $Ca_{10}(PO_4)_4(SiO_4)_2$), the process comprising: providing calcium or a calcium-containing compound, a phosphorus-containing compound and a silicon-containing compound; and forming a precipitate by reacting the compounds in an aqueous phase at an alkali pH.

20 Claims, 2 Drawing Sheets

(56) References Cited

OTHER PUBLICATIONS

Dickens, et al, "Crystal Structure of Ca3(PO4)2SiO4 (Silico-Carnotite)", TMPM Tschermaks Mineral Petror Mitt. 16, 1971; (pp. 1-27).
F. Balas, et al, "In Vitro Bioactivity of Silicon-substituted Hydroxyapatite", J. Biomed. Mater. Res. 66A (2003) (pp. 364-375).
S.R. Kim, et al, "Synthesis of Si, Mg Substituted Hydroxyapatites and Their Sintering Behaviors", Biomaterials 24 (2003) [pp. 1389-1398].
H-W Lee, et al, "Properties of Hydration and Strength of Sol-gel Derived Fine Particles in the System CaO-P2O5-Si02"; Journal of the Korean Ceramic Society, vol. 31, No. 10 (1994) (pp. 1231-1239) **English Language Abstract Only*.
M.W. Barnes, et al, "Hydration in the System Ca2SiO4-Ca3(PO4)2 At 90°C"; Journal of the American Ceramic Society 75[6] (1992) [pp. 1423-1429].
Arcos, et al, "Silicon Incorporation in Hydroxylapatite Obtained by Controlled Crystallization", Chemistry of Materials, American Chemical Society, vol. 16, No. 11, Jun. 1, 2004 (pp. 2300-2308).
Vallet-Regi, et al, "Silicon Substituted Hydroxyapatites. A Method to Upgrade Calcium Phosphate Based Implants"; Journal of Materials Chemistry, The Royal Society of Chemistry, vol. 15, No. 15, Apr. 21, 2005 (pp, 1509-1516).
Search Report issued Jun. 25, 2009 in related application No. GB0800335.2 (1 pg.).
ISR issued by the ISA/EP on Aug. 10, 2009 in related application No. PCT/GB2009/000059 (2 pgs).

* cited by examiner

SYNTHESIS OF BIOCERAMIC COMPOSITIONS

The present invention relates to biomedical materials and, in particular, to calcium phosphate based bioceramics.

The combined effects of an ageing population and greater expectations in the quality of life have resulted in an increasing global demand for orthopaedic implants for the replacement or augmentation of damaged bones and joints. In bone grafting current gold standards include the use of autograft and allograft but these methods are increasingly recognised as non-ideal due to limitations in supply and consistency. Ceramics have been considered for use as bone graft substitutes to replace or extend traditional bone grafts for over 30 years. In particular, calcium phosphates such as hydroxyapatite have been promoted as a result of their osteoinductive properties.

Accordingly, as surgical technique and medical knowledge continue to advance, there has been a growth in the demand for synthetic bone replacement materials. Consequently, there is an increasing interest in the development of synthetic bone replacement materials for the filling of both load bearing and non-load bearing osseous defects, such as in joint and facial reconstruction.

The biocompatibility of hydroxyapatite, coupled with the similarities between the crystal structure of hydroxyapatite and the mineral content of bone, has led to great interest in hydroxyapatite as a material for the augmentation of osseous defects. The apatite group of minerals is based on calcium phosphate, with stoichiometric hydroxyapatite having a molar ratio of Ca/P of 1.67. Hydroxyapatite has the chemical formula $Ca_{10}(PO_4)_6(OH)_2$.

Silicate (or silicon) substituted hydroxyapatite compositions provide attractive alternatives to stoichiometric hydroxyapatite as a bone replacement material, as the presence of silicate ions in the hydroxyapatite lattice appears to enhance bone cell behaviour, and accelerate bone repair. The substitution of silicate (or silicon) into the hydroxyapatite does have a compositional limit; when the level of silicate substitution passes this limit, the hydroxyapatite becomes thermally unstable at typical sintering temperatures of about 1200° C., and secondary phases such as tricalcium phosphate are formed. The substitution limit for silicate substitution into the hydroxyapatite lattice is approximately 5.3 wt % (or 1.6 wt % silicon). PCT/GB97/02325 describes a substituted hydroxyapatite material.

For the avoidance of doubt, the term silicate-substituted as used herein also encompasses silicon-substituted. Likewise, silicon-substituted as used herein also encompasses silicate-substituted.

Silicate substitution in hydroxyapatite can be described by the composition:

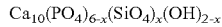
$Ca_{10}(PO_4)_{6-x}(SiO_4)_x(OH)_{2-x}$

The actual compositions that remain as a single, pure hydroxyapatite-like phase upon sintering, such that they form ceramics, are limited to a value of approximately x=0.6. For higher values of x, multiphase compositions are obtained.

When x=2.0, the composition is described as:

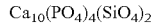
$Ca_{10}(PO_4)_4(SiO_4)_2$

This specific phase is described as calcium silico-phosphate (termed CPS), or by the mineral name silicocarnotite. The structure of this material, prepared by a solid state method, was reported by Dickens et al (B. Dickens, W. E. Brown, "Crystal structure of silicocarnotite", Tschermakis Mineral Petrogr Mitt 1971; 16: 1-27). A more recent synthesis, using hydrothermal synthesis, was described by Balas et al, where they used the final product as an X-ray Photoelectron Spectroscopy (XPS) reference material (F. Balas et al, "In vitro bioactivity of silicon-substituted hydroxyapatite", J. Biomed. Mater. Res. 66A (2003) 364-375). Kim et al observed the formation of a CPS phase in a silicon-substituted hydroxyapatite composition containing 3.76 wt % Si (corresponding to x=1.3 in $Ca_{10}(PO_4)_{6-x}(SiO_4)_x OH_{2-x}$) (S. R. Kim et al, "Synthesis of Si, Mg-substituted hydroxyapatites and their sintering behaviour", Biomaterials 24 (2003) 1389-1398). The maximum amount of CPS phase formed, however, was less that 30%.

H-W. Lee and J-H Kim, Korean Ceramic Academy Society 31 (1994) "Properties of Hydration and Strength of Sol-gel derived fine particles in the system $CaO—P_2O_5—SiO_2$"; M. W. Barnes et al, "Hydration in the system $Ca_2SiO_4—Ca_3(PO_4)_2$ at 90° C.", J. Am. Ceram. Soc. 75[6] (1992) 1423-1429. describe the formation of a calcium silico-phosphate, or silicocarnotite, phase with hydraulic bone cement systems, which are low temperature reaction systems.

U.S. Pat. No. 4,612,053 relates to combinations of sparingly soluble calcium phosphates as remineralizers of caries lesions in dental enamel and partially demineralized dentin and cementum and in their application as dental cements.

JP 3023245 and JP 3033059 relate to a low-cost hydraulic cement compositions.

U.S. Pat. No. 6,342,547 relates to an epoxy resin composition for an $SF_6$-gas insulating device which is obtained by adding a silicate compound powder to an epoxy resin.

JP 4022003 and JP 4022004 relate to an electric insulating member with high heat resistance and high electric insulating characteristics and which is composed of a complex of inorganic fibers and a curing hydrate of a calcium phosphate compound.

The present invention describes the synthesis, using an aqueous precipitation reaction, of a composition that, on controlled sintering/heat-treatment, contains calcium silico-phosphate, or silicocarnotite (and termed CPS), as the major phase, for use as a bioceramic implant material.

This synthesis reaction, and subsequent heat-treatment is suitable to produce industrial scale quantities of this bioceramic composition.

Accordingly, in a first aspect, the present invention provides a process for the synthesis of a bioceramic composition comprising calcium phosphosilicate (CPS, $Ca_{10}(PO_4)_4(SiO_4)_2$), the process comprising:

providing calcium or a calcium-containing compound, a phosphorus-containing compound and a silicon-containing compound; and forming a precipitate by reacting the compounds in an aqueous phase at an alkali pH.

The process may be used to produce a composition as herein described with reference to any of the other aspects according to the present invention.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The calcium phosphosilicate (CPS) is preferably present in the composition as the predominant phase and is preferably present in an amount of 50 wt. % or more, more preferably 60 wt. % or more, still more preferably 70 wt. % or more, still more preferably 80 wt. % or more.

The inventors have found that in order to obtain a high yield of CPS, the molar ratio of calcium to phosphate+silicate is advantageously chosen to be about 10:6. For the same reason, the molar ratio of phosphate to silicate is advantageously chosen to be from about 5:1 to about 4:2. In a preferred embodiment, the molar ratio of phosphate to silicate is from about 4.2:1.8 to about 4:2, relative to 10 moles of calcium.

The calcium-containing compound is preferably a calcium salt and may, for example, be selected from one or more of calcium hydroxide, calcium chloride, calcium nitrate and/or calcium nitrate hydrate.

The phosphorus-containing compound is preferably selected from one or both of a phosphate salt and/or a phosphoric acid, more preferably from one or both of ammonium phosphate and/or phosphoric acid.

The silicon-containing compound is preferably a silicate and may, for example, be selected from one or both of tetraethyl orthosilicate (TEOS) and/or silicon acetate.

The silicate is preferably present in the material in an amount of up to 20 weight percent, more preferably from 12 and 20 weight percent, still more preferably from 17 and 20 weight percent.

The aqueous precipitation step or steps are preferably carried out at an alkali pH. In order to optimise the yield of CPS, the inventors have found that the pH is preferably from 8 to 13, more preferably from 10 to 12.

An alkali may be added to adjust the pH of the solution to the desired pH. A suitable example is ammonium hydroxide.

The aqueous precipitation method according to the present invention may be carried out at room temperature (typically from 20 to 30° C.).

After the precipitate has been formed it is preferably heated to a temperature in the range of from 1000° C. to 1600° C., more preferably from 1100° C. to 1500° C., still more preferably from 1200° C. to 1300° C. The material is preferably sintered at these temperatures. The inventors have found that sintering within these temperature ranges increases the yield of CPS.

The precipitate is preferably heated for a periods of from 1 to 120 hours, more preferably from 2 to 32 hours, still more preferably from 4 to 16 hours. This preferred heating time is significantly longer than conventional times used to sinter hydroxyapatite or silicate-substituted hydroxyapatite ceramics, as long sintering times of greater than 1-2 hours lead to an increase in grain size of the ceramics, a reduction in strength and an increase in manufacturing costs. However, in the case of the present invention, the inventors have found that prolonged sintering/heating times of at least 2 hours leads to the formation of greater quantities of the CPS phase, at the expense of a hydroxyapatite-like phase and an alpha-tricalcium phosphate-like phase. The heating step will typically result in sintering of the material.

The process may further comprise cooling the sample from the heating temperature and optionally carrying out a post-heating annealing step. These additional steps are useful because they facilitate the transformation of any alpha-tricalcium phosphate secondary phase to a beta-tricalcium phosphate if desired.

The bioceramic composition may also contain an amorphous phase as a minor component (typically less than 2 wt. %). The bioceramic composition may also contain unavoidable impurities (typically less than 1 wt. %).

In a second aspect, the present invention provides a synthetic bioceramic composition comprising calcium phosphosilicate (CPS, $Ca_{10}(PO_4)_4(SiO_4)_2$), the composition being obtained by a process comprising:

an aqueous precipitation step or steps involving mixing calcium or a calcium-containing compound, a phosphorus-containing compound and a silicon-containing compound; and heating the collected product produced by the aqueous precipitation step or steps.

In one embodiment, the synthetic bioceramic composition comprises calcium phosphosilicate as the predominant phase together with one or more secondary, minor phases such as, for example, hydroxyapatite, silicate-substituted hydroxyapatite, alpha-tricalcium phosphate, beta-tricalcium phosphate, brushite, monetite, tetracalcium phosphate, octacalcium phosphate, calcium pyrophosphate, calcium silicate, calcium oxide, calcium carbonate, amorphous calcium phosphate glass, amorphous calcium silicate glass, and/or amorphous calcium phospho-silicate glass.

The calcium phosphosilicate phase may constitute from 50 to 98 wt. % of the total crystalline phase composition, preferably from 70 to 98%, more preferably from 90 to 98%. The remainder of the composition may, for example, be composed of one or more of the secondary, minor phases as described above. Accordingly, the synthetic bioceramic composition may contain, for example, from 2 to 30 wt. % of one or more of these secondary, minor phases. The preferred minor phases comprise one or more of hydroxyapatite, silicate-substituted hydroxyapatite, alpha-tricalcium phosphate and/or beta-tricalcium phosphate.

The presence of the above-described secondary phases may be desirable because they affect the rate at which calcium and phosphate ions become available in vivo.

In one preferred embodiment, the calcium phosphosilicate phase constitutes approximately 98 (±2) wt. % of the total crystalline phase composition.

In another preferred embodiment of the present invention, there is provided a synthetic bioceramic composition comprising calcium phosphosilicate (CPS) as the predominant phase, wherein the secondary phase comprises hydroxyapatite and/or a hydroxyapatite-like phase. Hydroxyapatite-like phase is intended to encompass, for example, silicate-substituted hydroxyapatite. The calcium phosphosilicate may constitute 70 to 98 wt. % of the composition, more preferably 80 to 98 wt. %. The secondary phase may constitute from 2 to 30 wt. % of the composition, more preferably 2 to 20 wt. %. Small amounts (typically <1 wt. %) of unavoidable impurities may also be present.

In another preferred embodiment of the present invention, there is provided a synthetic bioceramic composition comprising calcium phosphosilicate (CPS) as the predominant phase, wherein the secondary phase comprises one or more of alpha-tricalcium phosphate, an alpha-tricalcium phosphate-like phase, beta-tricalcium phosphate and/or a beta-tricalcium phosphate-like phase. The calcium phosphosilicate may constitute 70 to 98 wt. % of the composition, more preferably 80 to 98 wt. %. The secondary phase may constitute from 2 to 30 wt. % of the composition, more preferably 2 to 20 wt. %. Small amounts (typically <1 wt. %) of unavoidable impurities may also be present.

In another preferred embodiment of the present invention, there is provided a synthetic bioceramic composition comprising calcium phosphosilicate (CPS) as the predominant phase, wherein the secondary phase comprises: (i) hydroxyapatite and/or a hydroxyapatite-like phase; and one or both of (ii) alpha-tricalcium phosphate and/or alpha-tricalcium phosphate-like phase; and/or (iii) beta-tricalcium phosphate and/or beta-tricalcium phosphate-like phase. The calcium phosphosilicate may constitute 70 to 98 wt. % of the composition, more preferably 80 to 98 wt. %. The secondary phase may constitute from 2 to 30 wt. % of the composition, more preferably 2 to 20 wt. %. Small amounts (typically <1 wt. %) of unavoidable impurities may also be present.

As noted above, the presence of the above-described secondary phases may be desirable because they affect the rate at which calcium and phosphate ions become available in vivo. For example, alpha-tricalcium phosphate is more soluble than CPS and will therefore render calcium and phosphate ions more quickly.

The present invention also provides for a synthetic bone material, bone implant, orthopaedic implant, tissue implant, bone graft, bone substitute, bone scaffold, filler, coating or cement comprising a composition as herein described. The present invention also provides for the use of the compositions as herein described in these applications. The present invention also provides for a method of treating a patient, the method comprising delivering a bioceramic composition as herein described to a site in the patient to be treated. The present invention also provides a bioceramic composition as herein described for use as a biomedical implant. The present invention also provides a bioceramic composition as herein described for use in therapy. The present invention also provides a bioceramic composition as herein described for use in reconstructive or replacement surgery.

It will be appreciated that bioceramic composition as herein described may be used in these biomedical applications on its own or in conjunction with one or more of a biocompatible polymer, other type of ceramic, glass, and/or glass-ceramic material.

The present invention will now be described further, by way of example, with reference to the following non-limiting examples and the accompanying drawings in which.

EXAMPLE 1

Figure 1:
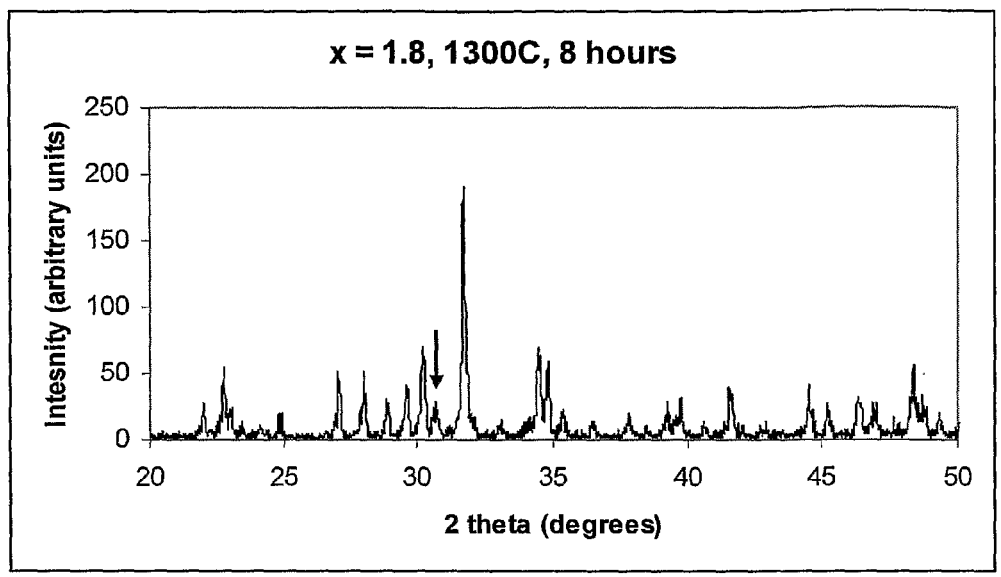
FIG. 1 is an X-ray diffraction pattern of the calcium silicophosphate composition CPS-1.8 (x=1.8, pH 12) sintered at 1300° C. for 8 hours (arrow indicates alpha-TCP as a minor second phase, with all other peaks corresponding to CPS phase)

Synthesis of a Bioceramic with Calcium Silicophosphate (CPS) as the Main Phase (x=1.8)

The starting materials for the synthesis were as described in Table 1.

TABLE 1

Starting reagents used to synthesise a bioceramic
with Calcium Silicophosphate (CPS) as the main phase.

| | |
|---|---|
| $CaCO_3$ | (99+% Sigma-Aldrich) |
| $H_3PO_4$ | (85 wt % Sigma-Aldrich) |
| TEOS | (98% Sigma Aldrich) |

Small batches of the novel materials of approximately 10 grams were prepared. Calcium carbonate powder was decarbonated for 24 hours prior to synthesis to produce calcium oxide, by placing the powder in a silica crucible and heating at 900° C. in a furnace. The calcium oxide powder was added to 200 mL of distilled water to form a hydrated calcium hydroxide solution. Prepared solutions of orthophosphoric acid and tetraethylorthosilicate (TEOS) were then added (together) drop wise with continuous stirring. In a similar synthesis, the orthophosphoric acid and tetraethylorthosilicate solutions were added separately. The pH was adjusted to the required level during the addition of the $H_3PO_4$/TEOS solution by the addition of a suitable base, such as ammonia solution, sodium hydroxide or potassium hydroxide. The precipitate was then covered and stirred for a further hour before leaving to stand overnight. The precipitate was then filtered using a Buchner funnel and vacuum pump. It was removed from the funnel and allowed to dry in a drying oven at around 80° C. for 24 hours.

The following equation represents the formula for calcium silicophosphate (CPS):

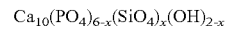

$$Ca_{10}(PO_4)_{6-x}(SiO_4)_x(OH)_{2-x}$$

where x is equal to the level of doping.

A range of compositions were prepared with values of x ranging from 1.4 to 2.4. It was found that the optimum range in terms of CPS yield was between 1.6 and 2.2, and most preferably 1.8-2.0.

For x=2.0, the formula becomes $Ca_{10}(PO_4)_4(SiO_4)_2$, equivalent to $Ca_5(PO_4)_2(SiO_4)$, the reported CPS phase which contains no hydroxyl groups. The x values were calculated as outlined in the example below.

For x=1.8 (CPS-1.8) the following equation can be written:

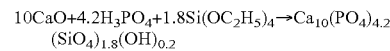

$$10CaO + 4.2H_3PO_4 + 1.8Si(OC_2H_5)_4 \rightarrow Ca_{10}(PO_4)_{4.2}(SiO_4)_{1.8}(OH)_{0.2}$$

The above equation is true, provided that synthesis pH is ≥8.

Divide by a factor of 100 (because only 10 g is required) to give:

0.1 moles of CaO=5.6079 g
0.042 moles of $H_3PO_4$=4.842 g (adjusted to compensate for 85 wt % starting material)
0.018 moles of TEOS=3.750 g When synthesising larger batches, for example 50 g, the dividing factor is reduced to 20 to give the masses of reactants required.

The synthesis for each x value was repeated 3 times but at pH values of 8, 10 and 12. The pH was monitored during the synthesis using a pH meter. The pH was adjusted using ammonia solution and nitric acid as required. The pH was monitored until most of the orthophosphoric acid/TEOS solution had been added, and was then adjusted accordingly until the synthesis was complete. It has been found that an alkali pH of from 8 to 12 provides a good yield of CPS.

The synthesis of the samples at all x values and all pHs was repeated, but with the addition of orthophosphoric acid being made before the addition of TEOS. It was decided not to use this method for the main syntheses as it is possible that after addition of orthophosphoric acid, the stoichiometric HA may form preferentially and impede the inclusion of silicate. By adding the two solutions together (the preferred method) it is believed that the intended stoichiometry (Si/P) would remain.

All filtered and dried samples were sintered as powders in platinum boats in a furnace. The temperature was raised by 5° C. per minute until the target temperature was reached. The temperature was then held at this temperature for a given period of time before cooling to 25° C. at a rate of 10° C. per minute.

Sintering was carried out at 1100, 1200 and 1300° C. for times of 2, 4, 8 and 16 hours in order to monitor the development of phase compositions under these different conditions.

Samples underwent phase characterisation using an X-ray diffractometer with Cu Kα radiation, λ=1.5418 Å. Phase analysis was carried out on each sample to determine the phase composition of the sintered sample. This was done using EVA software and standard patterns from the powder diffraction file.

To calculate the percentage compositions of the samples a commercial quantitative phase analysis technique was used (TOPAS), which determined the relative amounts of the crystalline phases present from the X-ray diffraction data.

For a sample with x=1.8 (CPS-1.8), prepared at pH=12, and sintered at 1300° C. for 8 hours, the major phase was calcium silicophosphate (CPS), with alpha-tricalcium phosphate present as a minor phase; the phase composition determined from quantitative phase analysis of the X-ray diffraction data is listed in Table 2.

TABLE 2

The phase composition determined from quantitative phase analysis of a composition with x = 1.8, pH = 12, sintered at 1300° C. for 8 hours (CPS-1.8).

| | |
|---|---|
| Calcium silicophosphate (CPS) | 89% |
| alpha-tricalcium phosphate | 11% |

Chemical analysis of this composition was performed using XRF and the results are listed in Table 3. The Ca/(P+Si) molar ratio is slightly less than the designed composition of 1.67, and this is consistent with the small amount of a-TCP observed by X-ray diffraction.

TABLE 3

Chemical compositions, determined from XRF analysis, of a composition with x = 1.8, pH = 10, sintered at 1300° C. for 8 hours (CPS-1.8).

| | |
|---|---|
| CaO (wt %) | 57.64% |
| P2O5 (wt %) | 31.92% |
| SiO2 (wt %) | 10.5% |
| Si (wt %) | 4.9 |
| Ca/(P + Si) | 1.65 |

The final composition described in Table 2 was designed to have calcium silicophosphate (CPS) as the major phase, with the biologically active alpha-tricalcium phosphate being present as a minor phase. The presence of this well-characterised calcium phosphate phase as minor second phase enhances the biological behaviour of this bioceramic composition in certain applications.

Figure 2:
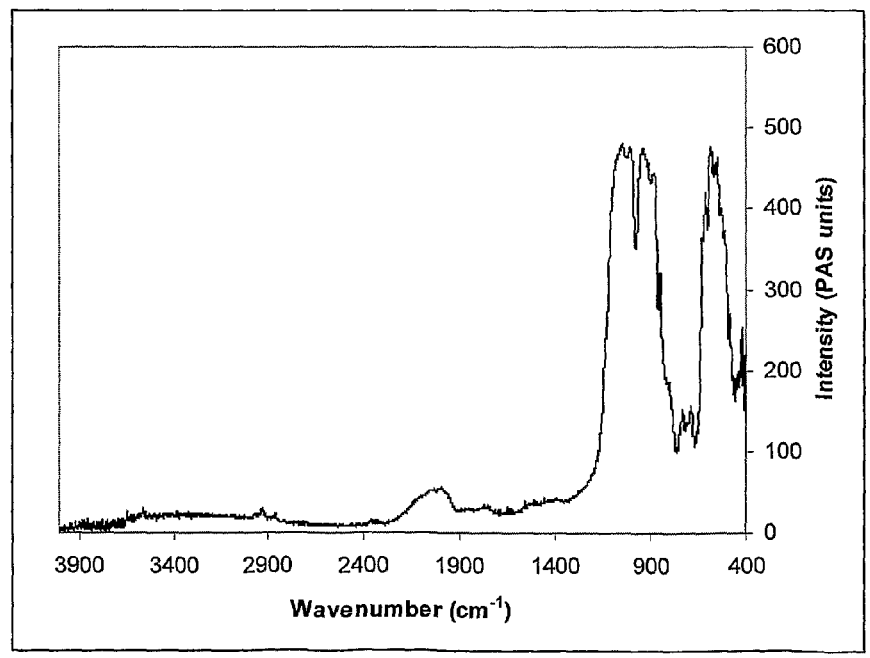
FIG. 2 is a Fourier Transform Infra-red (FTIR) spectrum, obtained using a PAS cell, of the calcium silicophosphate composition CPS-1.8 (x=1.8, pH 12) sintered at 1300° C. for 8 hours.

The X-ray diffraction pattern of the composition with x=1.8, pH=12, sintered at 1300° C. for 8 hours (CPS-1.8) is shown in FIG. 1, and the corresponding Fourier Transform Infrared (FTIR) spectrum is shown in FIG. 2.

Figure 3:
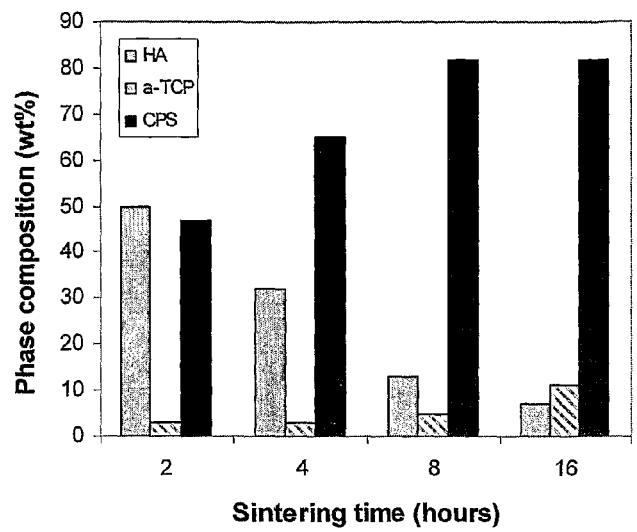
FIG. 3 shows the effect of sintering time on the phase composition of the calcium silicophosphate composition CPS-2.0 (x=2.0, pH 12) sintered at 1200° C.

The effect of increasing the sintering time from 2 to 16 hours on the phase composition of samples sintered at 1200° C. is shown in FIG. 3. Increasing the sintering time resulted in a decrease in the amount of a hydroxyapatite-like phase and a surprisingly large increase in the amount of CPS phase, such that after 2 hours it is present in equal proportions to the hydroxyapatite-like phase, whereas after 8 or 16 hours the CPS phase is the predominant phase. By contrast, sintering a single phase hydroxyapatite or a silicate-substituted hydroxyapatite samples would not result in any change in phase composition with prolonged sintering/heating time at 1200° C.

The FTIR spectra shows characteristic peaks corresponding to phosphate and silicate groups, and the absence of any significant peak corresponding to hydroxyl groups at ~3570 cm-1, showing that this composition contains predominantly the calcium silicophosphate (CPS) phase.

The effect of soaking the composition with x=1.8, pH=12, sintered at 1300° C. for 8 hours (CPS-1.8) in a TRIS-buffer at pH 7.4 and 37° C. for 120 hours, as described by ISO 10993-14 showed that the pH of the soaking solution increase from 7.4 to 7.95 (SD=0.03), whereas a single-phase hydroxyapatite samples showed only a small increase in pH from 7.4 to 7.58 (SD=0.02) over the same soaking period. The weight loss of the samples with composition with x=1.8, pH=12, sintered at 1300° C. for 8 hours (CPS-1.8) was 2.21% (SD=0.33), whereas the single-phase hydroxyapatite samples showed a larger decrease in weight of 4.95% (SD=0.33) over the same time period. The sample with composition CPS-1.8 actually showed evidence by scanning electron microscopy (SEM) of the precipitation of a calcium phosphate apatite-like phase on the surface of the soaked granules, which is consistent with the decrease in sample mass (dissolution of Ca and PO4 ions into solution) and the increase in pH (which favours the precipitation of a surface apatite-like layer). The single-phase hydroxyapatite samples did not show any evidence by SEM of the precipitation of an apatite-like phase on the surface of the samples.

EXAMPLE 2

Synthesis of a Bioceramic with Calcium Silicophosphate (CPS) as the Main Phase (x=2.0)

For x=2.0 (CPS-2.0) the following equation can be written:

$$10CaO + 4H_3PO_4 + 2Si(OC_2H_5)_4 \rightarrow Ca_{10}(PO_4)_4(SiO_4)_2$$

The above equation is true, provided that synthesis pH is ≥8.

Divide by a factor of 100 (because only 10 g is required) to give:

0.1 moles of CaO=5.6079 g 0.04 moles of $H_3PO_4$=4.842 g (adjusted to compensate for 85 wt % starting material)

0.02 moles of TEOS=3.750 g

When synthesising larger batches, for example 50 g, the dividing factor is reduced to 20 to give the masses of reactants required.

The synthesis and characterisation of samples with x=2.0 were performed as described in Example 1, for x=1.8.

The phase composition of sample CPS-2.0 after sintering at 1300° C. for 8 hours, determined by quantitative phase analysis of the X-ray diffraction data, is listed in Table 4. The composition consists of calcium silicophosphate as the predominant phase, with a small amount of alpha-TCP as a second phase; the amount of alpha-TCP in the CPS-2.0 sample was less than considerably less than that observed in the CPS-1.8 sample (11%, Table 2).

TABLE 4

The phase composition determined from quantitative phase analysis of a composition with x = 2.0, pH = 12, sintered at 1300° C. for 8 hours (CPS-2.0).

| | |
|---|---|
| Calcium silicophosphate (CPS) | 98% |
| alpha-tricalcium phosphate | 2% |

Chemical analysis of this composition was performed using XRF and the results are listed in Table 5. The amount of Si incorporated is greater than observed for composition x=1.8, as would be expected. Again, the Ca/(P+Si) molar ratio is slightly less than the designed composition of 1.67, and this is consistent with the small amount of a-TCP observed by X-ray diffraction.

TABLE 5

Chemical compositions, determined from XRF analysis, of a composition with x = 2.0, pH = 12, sintered at 1300° C. for 8 hours (CPS-2.0).

| | |
|---|---|
| CaO (wt %) | 57.78% |
| P2O5 (wt %) | 30.65% |
| SiO2 (wt %) | 11.7% |
| Si (wt %) | 5.5 |
| Ca/(P + Si) | 1.64 |

Figure 4:
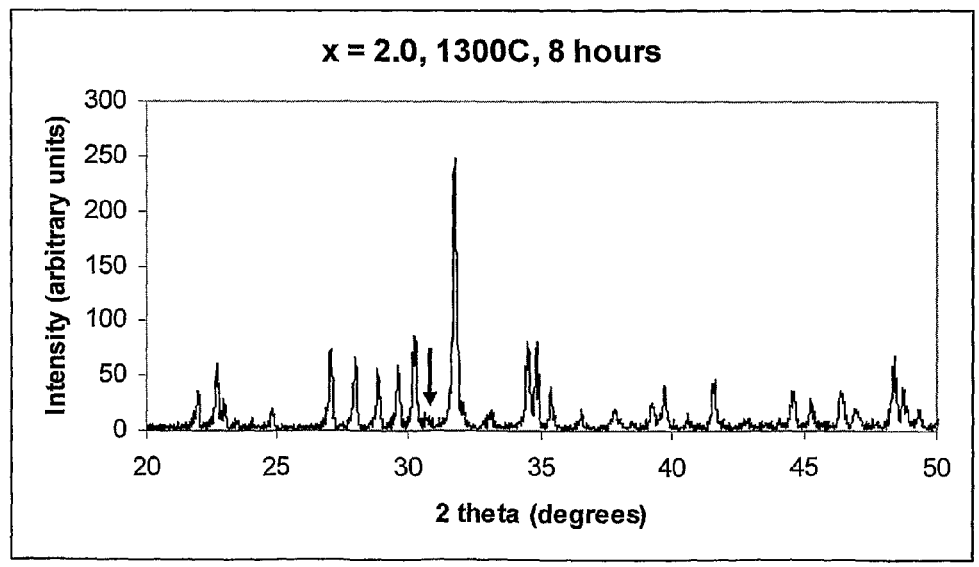
FIG. 4 is an X-ray diffraction pattern of the calcium silicophosphate composition CPS-2.0 (x=2.0, pH 12) sintered at 1300° C. for 8 hours (arrow indicates alpha-TCP as a minor second phase, with all other peaks corresponding to CPS phase).

The X-ray diffraction pattern of sample CPS-2.0, sintered at 1300° C. for 8 hours, is shown in FIG. 4.

The invention claimed is:

1. A process for the synthesis of a bioceramic composition for biomedical applications and comprising calcium phosphosilicate (CPS, $Ca_{10}(PO_4)_4(SiO_4)_2$), the process comprising:
   providing calcium or a calcium-containing compound, a phosphorus-containing compound and a silicon-containing compound;
   forming a precipitate by reacting the compounds in an aqueous phase at an alkali pH: and
   heating the precipitate either:
      at a temperature in the range of 1000° C. to 1300° C. for greater than two hours; or
      at a temperature in the range of 1300° C. to 1600° C. for at least one hour.

2. A process according to claim 1, wherein the calcium phosphosilicate (CPS) is present in the composition as the predominant phase and in an amount of 70 wt. % or more, preferably 80 wt. % or more.

3. A process according to claim 1, wherein the molar ratio of calcium to phosphate+silicate is about 10:6.

4. A process according to claim 1, wherein the molar ratio of phosphate to silicate in the bioceramic composition is from about 5:1 to about 4:2.

5. A process according to claim 4, wherein the molar ratio of phosphate to silicate in the bioceramic composition is from about 4.2:1.8 to about 4:2.

6. A process according to claim 1, wherein the calcium-containing compound is a calcium salt.

7. A process according to claim 6, wherein the calcium salt is selected from one or more of calcium hydroxide, calcium chloride, calcium nitrate and/or calcium nitrate hydrate.

8. A process according to claim 1, wherein the phosphorus-containing compound is selected from one or both of a phosphate salt and/or a phosphoric acid.

9. A process according to claim 8, wherein the phosphorus-containing compound is selected from one or both of ammonium phosphate and/or phosphoric acid.

10. A process according to claim 1, wherein the silicon-containing compound is a silicate.

11. A process according to claim 10, wherein the silicate is selected from one or both of tetraethyl orthosilicate (TEOS) and/or silicon acetate.

12. A process according to claim 10, wherein the silicate is present in the material in an amount of up to 20 weight percent, preferably from 12 to 20 weight percent, more preferably from 17 to 20 weight percent.

13. A process according to claim 1, wherein the pH is from 8 to 13.

14. A process according to claim 13, wherein the pH is from 10 to 12.

15. A process according to claim 1, wherein an alkali is added to adjust the pH of the solution to the desired pH.

16. A process according to claim 15, wherein the alkali is ammonium hydroxide.

17. A process according to claim 1, wherein after the precipitate has been formed it is heated to a temperature in the range of from 1000° C. to 1600° C.

18. A process according to claim 17, wherein the precipitate is heated to a temperature in the range of from 1100° C. to 1500° C., preferably from 1200° C. to 1300° C.

19. A process according to claim 17, wherein the precipitate is heated for a periods of from 1 to 120 hours, preferably from 2 to 32 hours, more preferably from 4 to 32 hours.

20. A process according to claim 17 further comprising cooling the sample from the heating temperature and optionally carrying out a post-heating annealing step.

* * * * *